(12) United States Patent  
Cornsweet et al.

(10) Patent No.: US 6,834,958 B2
(45) Date of Patent: Dec. 28, 2004

(54) INSTRUMENTS AND METHODS FOR EXAMINING AND QUANTIFYING CATARACTS

(75) Inventors: Tom N. Cornsweet, Prescott, AZ (US); Paul Peterson, Prescott, AZ (US)

(73) Assignee: Visual Pathways, Inc., Prescott, AZ (US)

( * ) Notice: Subject to any disclaimer, the term of this patent is extended or adjusted under 35 U.S.C. 154(b) by 70 days.

(21) Appl. No.: 10/201,870

(22) Filed: Jul. 23, 2002

(65) Prior Publication Data

US 2003/0058405 A1 Mar. 27, 2003

Related U.S. Application Data

(60) Provisional application No. 60/307,272, filed on Jul. 23, 2001.

(51) Int. Cl.[7] .............................. A61B 3/10; A61B 3/00
(52) U.S. Cl. ........................ 351/205; 351/221; 351/246
(58) Field of Search ................................ 351/200, 205, 351/206, 211, 213–216, 221, 246, 160 H; 600/318, 558

(56) References Cited

U.S. PATENT DOCUMENTS 3,915,564 A  10/1975  Urban ........................... 351/7
4,019,813 A  4/1977   Cornsweet et al. ........... 351/14

(List continued on next page.)

FOREIGN PATENT DOCUMENTS

EP     0231769    8/1987
EP     0337745    10/1989

OTHER PUBLICATIONS

Navarro, R. and Losada, M., "Phase transfer and point–spread function of the human eye determined by a new asymmetric double–pass method", Nov. 1995, vol. 12, No. 11, J. Opt. Soc. Am. A, pp. 2385–2392.

*Primary Examiner*—Brian L. Casler
*Assistant Examiner*—John R Sanders
(74) *Attorney, Agent, or Firm*—Cahill, von Hellens & Glazer P.L.C.

(57) ABSTRACT

A method is disclosed for quantifying the extent a cataract impairs vision in an eye having a pupil, an ocular lens, and a retina. The method includes illuminating a localized region of the retina such that light is reflected from the localized region and is transmitted through the ocular lens. A portion of the reflected light is scattered by the cataract associated with the ocular lens. Light reflected from the localized region of the retina is collected, and the amount of scatter is measured so as to quantify the extent the scatter impairs vision of the eye.

22 Claims, 8 Drawing Sheets

U.S. PATENT DOCUMENTS

| | | | |
|---|---|---|---|
| 4,187,014 A | 2/1980 | Kato et al. | 354/62 |
| 4,281,926 A | 8/1981 | Cornsweet | 356/124 |
| 4,283,124 A | 8/1981 | Matsumura | 351/7 |
| 4,329,049 A | 5/1982 | Rigg et al. | 356/124 |
| 4,405,215 A | 9/1983 | Sano et al. | 351/208 |
| 4,436,388 A | 3/1984 | Takahashi et al. | 351/206 |
| 4,469,416 A | 9/1984 | Isono | 351/206 |
| 4,579,430 A | 4/1986 | Bille | 351/206 |
| 4,715,703 A | 12/1987 | Cornsweet et al. | 351/205 |
| 4,993,827 A * | 2/1991 | Benedek et al. | 351/221 |
| 5,072,731 A * | 12/1991 | Taratuta et al. | 600/318 |
| 5,090,799 A | 2/1992 | Makino et al. | 351/221 |
| 5,114,222 A | 5/1992 | Cornsweet | 351/204 |
| 5,129,400 A | 7/1992 | Makino et al. | 128/666 |
| 5,196,872 A | 3/1993 | Beesmer et al. | 351/208 |
| 5,202,708 A | 4/1993 | Sasaki et al. | 351/206 |
| 5,210,554 A | 5/1993 | Cornsweet et al. | 351/206 |
| 5,233,517 A | 8/1993 | Jindra | 364/413.13 |
| 5,258,788 A * | 11/1993 | Furuya | 351/246 |
| 5,371,557 A | 12/1994 | Nanjho et al. | 351/206 |
| 5,382,988 A | 1/1995 | Nanjo | 351/206 |
| 5,410,376 A | 4/1995 | Cornsweet et al. | 351/210 |
| 5,422,690 A | 6/1995 | Rothberg et al. | 351/209 |
| 5,508,760 A | 4/1996 | Kobayashi et al. | 351/221 |
| 5,540,226 A * | 7/1996 | Thurston et al. | 600/558 |
| 5,542,422 A * | 8/1996 | Hayden | 600/318 |
| 5,572,266 A | 11/1996 | Ohtsuka | 396/18 |
| 5,579,063 A * | 11/1996 | Magnante et al. | 351/205 |
| 5,610,672 A * | 3/1997 | Hirono et al. | 351/205 |
| 5,684,561 A | 11/1997 | Yancey | 351/209 |
| 5,764,341 A | 6/1998 | Fujieda et al. | 351/221 |
| 5,844,658 A | 12/1998 | Kishida et al. | 351/206 |
| 5,885,224 A * | 3/1999 | Yoshida | 600/558 |
| 5,908,394 A * | 6/1999 | Kandel et al. | 600/558 |
| 5,912,720 A | 6/1999 | Berger et al. | 351/206 |
| 5,914,771 A | 6/1999 | Biber | 351/221 |
| 6,082,856 A * | 7/2000 | Dunn et al. | 351/160 H |
| 6,086,205 A | 7/2000 | Svetliza | 351/221 |
| 6,296,358 B1 | 10/2001 | Cornsweet et al. | 351/206 |
| 6,315,412 B1 * | 11/2001 | Snodderly et al. | 351/200 |
| 6,659,613 B2 * | 12/2003 | Applegate et al. | 351/221 |

* cited by examiner

INSTRUMENTS AND METHODS FOR EXAMINING AND QUANTIFYING CATARACTS

RELATED APPLICATION

This application claims priority under 35 U.S.C. §119(e) from U.S. Provisional Patent Application No. 60/307,272, filed Jul. 23, 2001, entitled "Instrument and Method for Examining and Quantifying Cataracts."

BACKGROUND OF THE INVENTION

1. Field of the Invention

The present invention relates generally to apparatus and methods for characterizing physical properties of an eye and more specifically for characterizing cataracts.

2. Description of the Related Art

The term cataract refers to a reduction in transparency of the lens within the eye. Although some cataracts develop rapidly, the vast majority develop over a period of decades, becoming increasingly prevalent in older populations. Surgery to remove cataractous lenses is currently a very common operation, performed by ophthalmologists, usually as an office procedure. This procedure typically includes the replacement of the cataractous lens with a plastic one, called an intraocular lens (IOL).

For virtually all cataracts, the physical process that reduces the transparency of the lens is not one that causes light absorption and thus opacity. Rather, the transparency is reduced because the material that forms the lens changes its structure in such a way that the lens scatters light. This light scatter impairs vision because it adds a veiling glare in the retinal image, reducing the contrast of the scene viewed.

Cataract surgery is not entirely without risk, and because cataracts usually develop so slowly, the question of when it is appropriate to perform the surgery to remove them is sometimes difficult. Surprisingly, as of this writing there is no widely accepted method, either subjective or objective, for determining when surgery is appropriate. One might expect that measures of visual acuity would be appropriate, but they have been shown not to be useful for making the decision about whether or not to undergo surgery. Methods currently used to evaluate cataracts for research on their prevention utilize a mixture of objective and subjective methods, namely, photographs taken using a standard ophthalmic instrument, the "slit lamp", are visually compared with a set of standardized photographs to pick which standard photograph looks most like the patient's.

Cataracts have long been observed by an optical method called retroillumination. With this method, the retina is illuminated, usually using a slit lamp, and the light reflected from the retina back-illuminates the lens in such a way that regions containing cataractous material appear darker than clear areas.

SUMMARY OF THE INVENTION

One aspect of the invention comprises a method of quantifying the extent a cataract impairs vision in an eye having a pupil, an ocular lens, and a retina. In this method a localized region of the retina is illuminated such that light is reflected from the localized region and is transmitted through the ocular lens. A portion of the reflected light is scattered by the cataract associated with the ocular lens. Light reflected from the localized region of the retina is collected, and the amount of scatter is measured so as to quantify the extent the scatter impairs vision of the eye.

In another aspect of the invention, a method of imaging cataracts in an eye having a cornea, a lens, a pupil, and a retina includes illuminating a localized region of the retina such that light is reflected from the localized region through the pupil of the eye. Light reflected from the localized region of the retina is collected with an optical element. An optical image of the eye is formed on a camera with the optical element so as to produce an electronic image of the eye. The electronic image of the eye is displayed on a monitor. The contrast of the optical image can be improved by minimizing the localized region of the retina that is illuminated.

Preferably, the electronic image is shown to the patient substantially simultaneously to the formation of the optical image on the camera. Additionally, the cataract is preferably characterized by quantifying scattering therefrom. Relative amounts of scatter can be computed for different portions of the electronic image of the eye and displayed on the monitor.

In another aspect of the invention, a method of imaging cataracts in an eye having a cornea, an ocular lens, and a retina comprises holding an assembly comprising a light source, imaging optics, and an optical detector array in place by hand a distance from the eye. A localized region of the retina is illuminated with light from the light source such that at least a portion of the light is reflected from the localized region of the retina through the ocular lens. Light reflected from the localized region of the retina is collected with an optical element. With the imaging optics, an optical image of the cataract is formed on the optical detector array so as to produce an electronic image of the cataract, and the electronic image of the cataract is displayed on a display.

Yet another aspect of the invention comprises an apparatus for imaging a cataract in an eye that includes a cornea, a pupil, a lens, and a retina. The apparatus comprises a light source, a first optical path from the light source to the eye, beam-shaping optics, imaging optics, an optical sensor, and a display. The beam-shaping optics is located in the first optical path so as to receive light emitted by the light source and direct it into the eye and onto the retina. The optical sensor is positioned in a second optical path from the eye to receive a portion of light from the light source reflected off the retina. The imaging optics is located in the second optical path at a position between the eye and the optical sensor so as to image the cataract onto the optical sensor. The display is in communication with the optical sensor to display an image of said eye. The light source is sufficiently small and the beam-shaping optics has a focal length sufficiently long such that light passing through the beam-shaping optics lens illuminates a spot on the retina between about 0.05 to 0.3 millimeters in size.

In still another aspect of the invention, an apparatus for imaging cataracts in an eye that includes a cornea, a pupil, a lens, and a retina comprises a hand-held optical assembly and a monitor. The hand-held optical assembly includes a light source, first and second lenses, a beamsplitter, and a camera. The first lens is located with respect to the light source to receive light emitted by the light source and direct it into the eye and onto the retina. The beamsplitter is inserted between the beam shaping lens and the eye such that the light passes through the beamsplitter to the eye. The camera is positioned to receive a portion of light from the light source reflected off the retina and reflected from the beamsplitter. The second lens is located at a position between the beamsplitter and the camera so as to image the eye onto the camera. The monitor is separate from and movable in relation to the optical assembly and is in communication with the camera to display an image of the eye.

DETAILED DESCRIPTION OF THE PREFERRED EMBODIMENT

Various preferred embodiments of instruments and methods described herein use retroillumination of the eye lens, in conjunction with a camera and a display device, and preferably a computer. The arrangement is preferably such that the patient and examiner can both observe a substantially live video or computer image of the patient's cataract, facilitating a discussion of the cataract between the examiner and patient. Automated quantification, for example of the extent and density, of the cataract is preferably performed to provide an objective criterion for deciding whether or not surgery is warranted.

Figure 1:
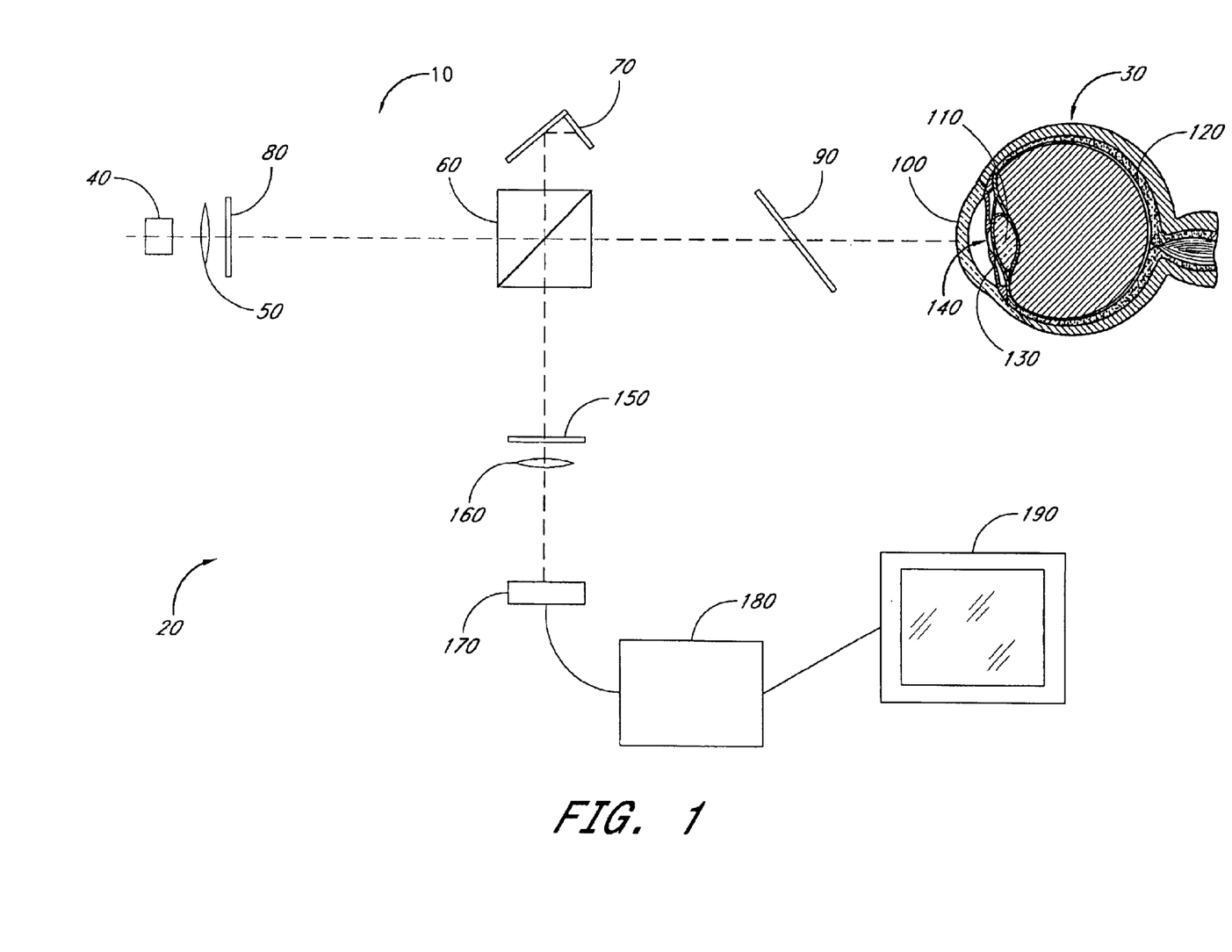
FIG. 1 depicts an instrument for imaging cataracts comprising a source of invisible radiation, first and second lenses, a beamsplitter and a camera, wherein the first lens is in a first arm between the source and the beamsplitter and the second lens is in a second arm between the beamsplitter and the camera.

FIG. 1 is a diagram of the optical components in an optical system 10 comprising one embodiment of an instrument 20 for characterizing an eye 30. Light from a source 40 of near infrared light, preferably an infrared-light-emitting diode (IRLED), passes through a first lens 50, which preferably substantially collimates, or at least substantially reduces the divergence of, the rays from the light source 40. A portion of that light is reflected from a beamsplitter 60, and is absorbed by a light trap 70. Another portion passes through the beamsplitter 60 and illuminates the front the eye 30. A linear polarizer, 80 whose function will be described below, lies between the light source 10 and the eye 30.

A filter 90 that passes the wavelengths emitted by the light source 40 but absorbs other wavelengths may optionally be inserted between the beamsplitter 80 and the eye 30. This filter 90 may perform several functions. It can be used to reduce ambient, i.e., room light, that might be detected and contribute to background noise, and it can serve as a window to prevent dust from entering the optical system 10. Additionally, the element 90 can also serve as a substitute for the polarizing elements to be described below, if for example it comprises a circular polarizer and a quarter-wave plate as well as a filtering component. A double pass through the quarter-wave plate rotates the polarization by about 90°.

The eye 30 is preferably that of a human subject, however, may be that of an animal subject. As is well known, the eye 30 includes a cornea 100, an ocular lens 110, a retina 120, and an iris 130. The iris 130 defines a pupil 140, which is a substantially circular or elliptical area between the cornea 100 and the ocular lens 110.

Some of the light incident on the eye 30 passes through the pupil 140, and the refractive actions of the cornea 100 and ocular lens 110 act on those rays to form an image of the source on the retina 120. Some of the light scattered from the retina 120 then passes back through the ocular lens 110, pupil 140, and cornea 100 and is incident on the beamsplitter 60. A portion of this scattered light is transmitted through the beamsplitter 60 and is lost as it progresses back toward the light source 40. Another portion is reflected by the beamsplitter 60, through a linear polarizer 150, and towards an imaging lens 160. The portion that is reflected by the beamsplitter 60 forms an optical image of the front of the eye 30 and the ocular lens 110 on the optically sensitive surface of a camera 170. This camera 170 may, for example, comprise a CCD array. The camera 170 preferably is electronically coupled to a computer or other electronics 180, which in turn is configured to send signals to a display device 190 such as a computer screen or television monitor for displaying an image of eye 30.

Figure 2:
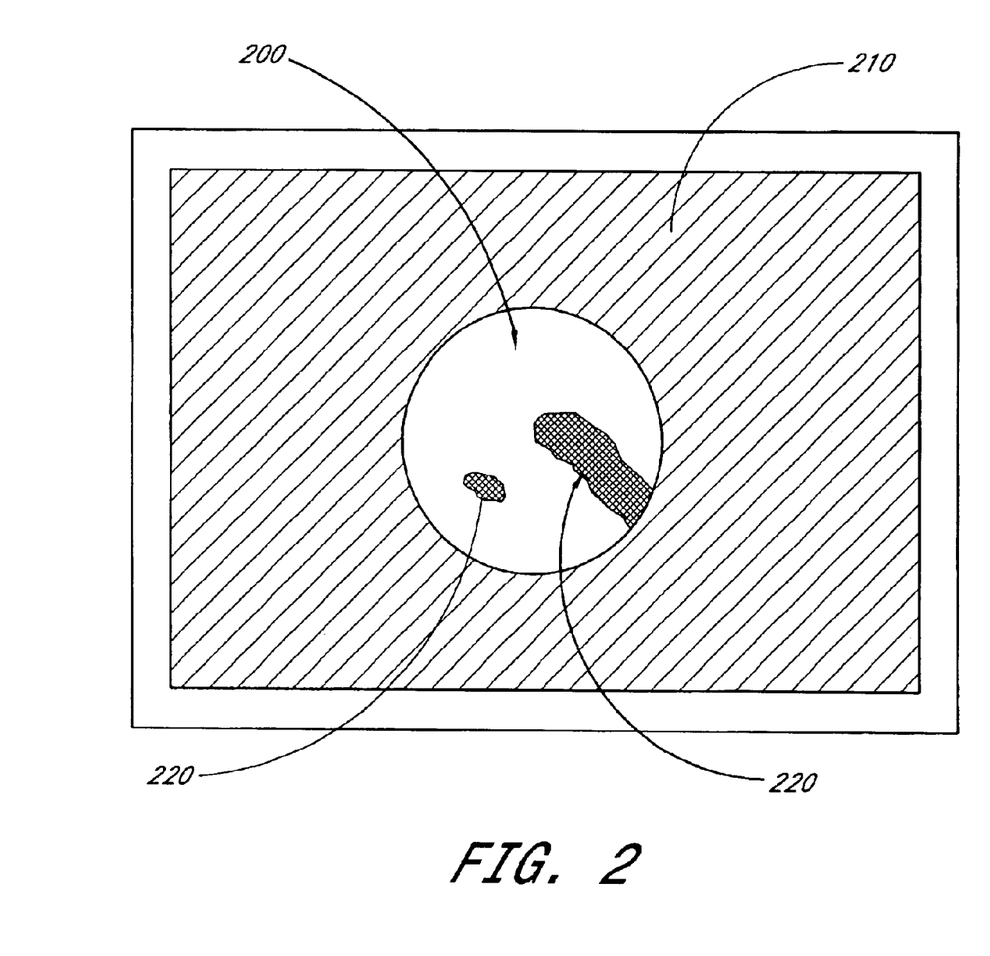
FIG. 2 shows an exemplary image of a cataractous ocular lens as seen by the video camera of FIG. 1.

FIG. 2 shows the appearance of an exemplary image produced by the camera 170 of an eye 30 with a cataract. A brighter region 200, corresponding to light passing through the pupil 140, is surrounded by a dark background 210. The presence of cataracts within the ocular lens 110 results in dark regions 220 within the brighter region 200 that corresponds to light passing through the pupil 140.

As described above, the lens 50 preferably provides a substantially collimated beam that is directed at the eye 30. Thus, if the eye 30 is preferably focused at infinity, the beam from the source 40 will be sharply focused on the retina 120, as the focal length of the cornea 100 and ocular lens 110 together ideally corresponds to the distance to the retina 120.

In one embodiment, the light source 40 comprises an IRLED with a microball lens, which provides an effective source size of about 0.05 millimeters (mm), i.e., an intermediate image comprising a small spot which is preferably located in the focal plane of the first lens 50. The focal length of the first lens 50 may be about 17 mm and its diameter may be about 10 mm. Accordingly, in one preferred embodiment, the distance from the effective source to the lens 50 is about 17 mm so as to direct a substantially collimated beam into the eye 30. With this arrangement, a nominal retinal image size of about 0.05 mm will be created for an emmetropic eye. The distance from the lens 50 to the beamsplitter 60 may be about 10 mm. The distance from the beamsplitter 60 to the eye 30 may be about 70 mm. The optical path from the eye 30 to the lens 160 may be about 200 mm as reflected through the beamsplitter 60, and the optical path from the lens 160 to the camera surface may be about 50 mm. This particular design should not be construed as limiting as other embodiments may include variations in dimensions, component specifications (e.g. optical power or focal length, numerical aperture or f-number, etc.), and designs beyond those explicitly recited above.

The first and second polarizers 80 and 150 may perform the following function. About 2% of the light incident on the eye 30 is reflected by the front surface of the cornea 100, and if that light were not eliminated, it would likely cause a bright spot to be superimposed on the image of the cataract. The polarizers 80 and 150, whose polarization axes lie substantially at right angle to each other, i.e. are substantially crossed, significantly reduce the intensity of this light reflected from a shiny surface, like the cornea 100.

If polarized light is reflected from a shiny surface, like the cornea 100, it retains its polarization, but if reflected from a matte surface like the retina 120, most polarization is lost. Thus, the light incident on the second polarizer 90 that is reflected from the retina 120 is relatively unpolarized, while the light reflected from the cornea 100 is strongly polarized. When this light is incident on the second polarizer 90, whose polarization axis is perpendicular to that of the first polarizer 90, the light from the cornea 100 is strongly blocked, thus eliminating the bright spot on the cataract image. Other arrangements for separating out the polarized light reflected from the cornea 100 may also be used and the possible designs are not limited to the arrangements recited herein.

In certain embodiments, the beamsplitter 60 also separates different polarizations, the light transmitted through the beamsplitter 60 being polarized in a plane perpendicular to the light reflected by the beamsplitter 60. Therefore, the polarizing action of beamsplitter 60 further reduces the reflection from the cornea 100. Sheet polarizers can be used as the first and second polarizers 80 and 90 and are relatively inexpensive. Relatively inexpensive beam-splitting cubes are also available. The method of separating out components of polarized light would also work, but at a higher cost, using, in the alternative, only a high-quality polarizing cube beamsplitter or using only high quality sheet polarizers. In other embodiments, the first linear polarizer 100 may be excluded, for example, in the case were the output of the light source 40 is linearly polarized.

Although the light source 40 is described above as an infrared LED, other types of light sources that operate in various wavelength ranges, including infrared, visible, or other wavelength ranges in the electromagnetic spectrum, can be employed as well. The light source 40 may or may not include built-in beam-shaping optics and/or filtering components.

In addition, the camera 30 may comprise a variety of types of optical detectors for receiving light contained in an optical image and producing a corresponding electronic signal suitable for use in displaying an associated image on a display device 190 such as a monitor or for input into a computer or other electronics 180. This optical detector may comprise a plurality or array of individual sensors or pixels that each receive a portion of a spatially distributed optical intensity pattern and that senses the localized intensity. In this manner, the sum of the pixels can together replicate the intensity distribution of the optical pattern incident on the optical detector. Examples of such optical detectors include, vidicon cameras and cameras based on charge coupled device (CCD) or a complementary metal oxide semiconductor (CMOS) array technology. The camera 30 may optionally include a built-in lens to form an integral package. In other embodiments, the camera 30 may be another type of device suitable for recording optical information such as a photographic camera based on a photosensitive emulsion on a film or plate. The camera 30 is not limited to those technologies disclosed herein. Thus, other embodiments may include new imaging technologies yet to be developed may be employed.

The display device 190 may include various devices suitable to receive a signal containing image information and that displays such image information in a format suitable for viewing. The signal may be received by the display device 190 from sources such as a camera 170, tape, antenna, computer, although is not limited to these. Examples of displays include television and computer screens and monitors, but should not be restricted to those recited herein.

As described above the display device 190 may receive input from electronics or a computer 180. These electronics may comprise a dedicated electronic device for processing information from the camera 170 and sending this information to the display device 190. In certain embodiments, the electronics may comprise components and circuitry for providing necessary functions such as memory storage, user inputs, and data output to a computer screen or monitor or printer, or other such display devices 190. In other embodiments, a commercially available desktop personal computer, laptop computer, or notebook computer may be employed. Other configuration and designs are also considered possible, and the display device 190 should not be restricted to those recited herein.

Also, the specific optical components employed should not be limited to the types described herein and depicted in the figures. For instance, the first and second lenses 50, 160 might be a compound lens made up of several elements used to improve image quality or diffractive elements. Other elements having optical power may be employed as well. These elements may be reflective, refractive, and/or diffractive optical elements well known in the art or yet to be devised. In some embodiments, the first lens 50 may be excluded if the output from the source 40 is suitable, e.g., is substantially collimated.

In various preferred embodiments, the optical components are selected and arranged so as to provide retroillumination of the ocular lens 110 and to produce an optical image of the eye 30 that can be used to quantify the amount of scattering produced by a cataract. A cataract that is more severe, i.e., that will impair vision more, will produce increased scattering and a corresponding darkening of the dark region 220 in the optical image of the eye 30.

Figure 3:
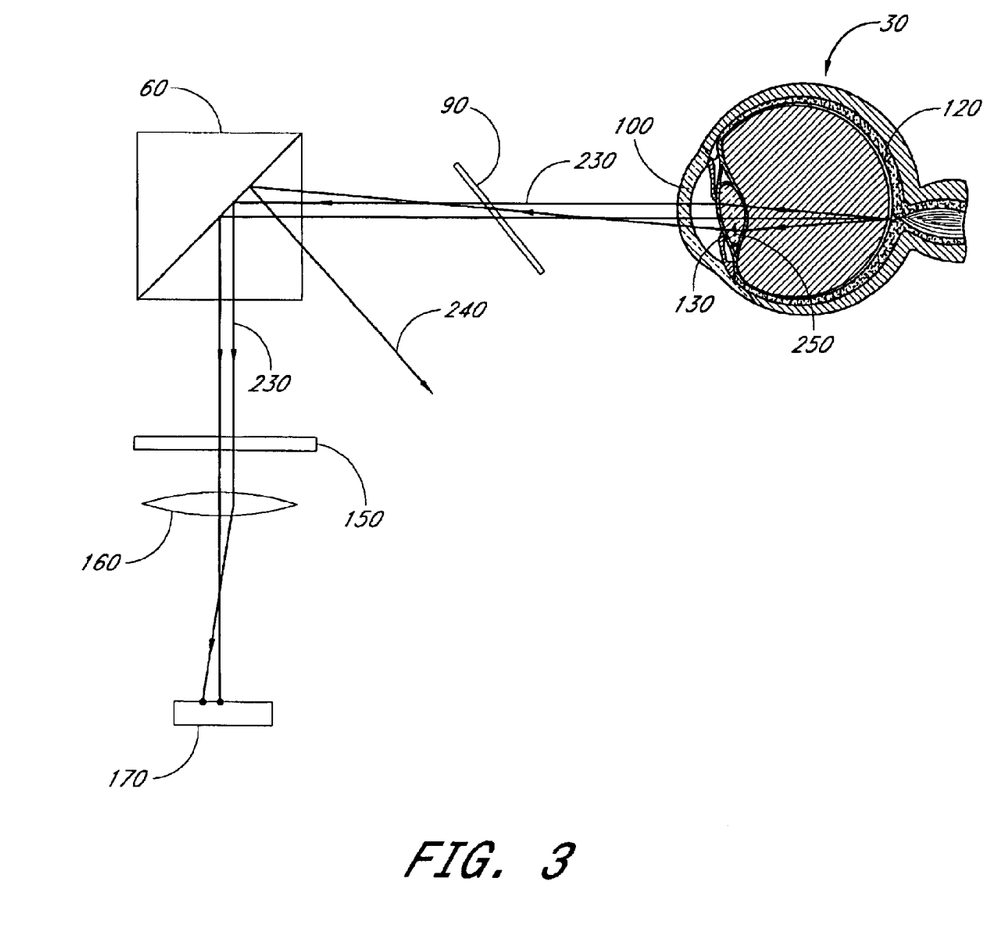
FIGS. 3 and 4 illustrates how a portion of the light scattered from the cataract does not reach the camera.

The reason why the cataractous region is darker in the image in FIG. 2 is illustrated in FIG. 3. Because light transmitted through the lens 50 is substantially collimated, it forms a preferably small bright point on the retina 120, which then acts as a light source. Some of the light emitted from this theoretical point source at the retina 120 is scattered as it is transmitted through the ocular lens 110 as discussed below.

Rays, such as ray 230, that pass through clear or nonscattering parts of the ocular lens 110 pass through the imaging lens 160 and illuminate the corresponding point in the image plane on the camera 170, as illustrated in FIG. 3. For example, rays passing through the top of the pupil 130 will converge on the bottom of the image of the pupil (i.e., the image lens 160 inverts the optical image) and rays passing through the bottom of the pupil will arrive at the top of the optical image in the process of image formation. However, rays such as ray 240 that are incident on a scattering region 250 of the ocular lens 110, are scattered and thus have an increased likelihood of missing the imaging lens 160 and not arriving at the corresponding region on the camera 170. Therefore, the regions 220 in the image corresponding to cataractous regions 250 of the ocular lens 110 receive less light and appear darker. Further, the stronger the scattering in the scattering region 250, the less light received at the corresponding point in the plane on the camera 170.

The amount of light falling on each point or pixel on the optical detector of the camera 170 is directly related to the degree to which the corresponding point on the ocular lens 110 scatters light. In other words, the brightness and darkness of each point in the optical image is directly related to the severity of the cataract at the corresponding location of the ocular lens 110. Many conventional optical detectors, such as for example CCDs and CMOS sensors, have a linear response to light, that is, the electrical signal generated in each pixel is directly proportional to the amount of light falling on the specific pixel on the detector, which may be mapped to a corresponding point on the display 190. Therefore, the electrical output (i.e., signals) from such a camera 170, when used with an optical arrangement such as in FIG. 1, will accurately represent the distribution of scattering points within the ocular lens 110 which can be presented in an image on the display.

It has been determined, however, that the size of the region on the retina 120 that is illuminated by the source 40 affects the quality of the image that is produced. In FIG. 3, the illuminated retinal region is shown as very small; it is approximated as a point source. Light reflected from the retina 120 incident on the scattering region 250 of the ocular lens 110 is scattered in many directions, so that some of this light arrives at the camera 170 but most does not. When a second small illuminated region is added, the accuracy of the measurement is reduced. Some of the light from the second small region that strikes the scattering region 250 of the ocular lens 110 is actually scattered along the same path as light from the first small region would follow if no scatterer were present. In other words, light from the second small region increases the amount of light falling on the image of the cataractous region 250, and thus reduces the darkness of the dark region 220 in the image thereby lowering the contrast. Accordingly, if the total region illuminated on the retina 120 is enlarged, which is, in effect, adding more small regions, the contrast of the resulting cataract image will be reduced and the measurement will be less accurate because the signal-to-noise ratio is lower. For this reason, the optics are preferably arranged so that the total illuminated region of the retina 120 is small.

To reduce the portion of the retina that is illuminated, the retinal image of the source 40 is preferably small, e.g., including but not limited to the range between about 0.05 and 0.3 mm. Accordingly, light emitting diodes are especially suitable as light sources. Alternatively, a small aperture can be placed in front of a larger light source 40, such as an incandescent bulb to limit the spatial extent of the source. The size of the light source 40 is preferably small in comparison to the focal length of the first lens 50.

Additionally, in embodiments described above, if a region of the ocular lens 110 scatters light coming from the retina 120, it will also scatter the light that is incident directly from the source 40. Some of that light will be scattered back toward the beamsplitter 60 and the camera 170, thus adding light in the very regions 220 that appear darker because of the scattering of light from the retina. If quantification of the cataract is to be correct, it is important that this back-scatter from the ocular lens 110 be taken into account.

Referring to FIG. 1, in principle, the beamsplitter 60 can be placed anywhere between the light source 40 and the eye 30, and imaging lens 160 is preferably placed somewhere between the beamsplitter 60 and the camera 170. Changing the imaging lens 160 location will of course require changing its focal length and/or the distance from the second lens 160 to the camera 170 to maintain the appropriate image size. However, the effect of the light back-scattered from the ocular lens 110 of the eye 30 can be made negligible if the distance between the eye and the imaging lens 160 is large, for the following reasons.

Light reflected from the retina 120 that passes through clear parts of the ocular lens 110 preferably emerges from the eye 30 in a beam. For example, if the illuminated region of the retina 120 is very small and the eye 30 is focused at infinity, then the beam will emerge approximately as a column of light whose diameter equals the diameter of the pupil 140, as shown by ray 260 and ray 270 in FIG. 4. If the eye 30 is not focused at infinity or if the illuminated region is larger, then the beam diverges proportionately.

Figure 4:
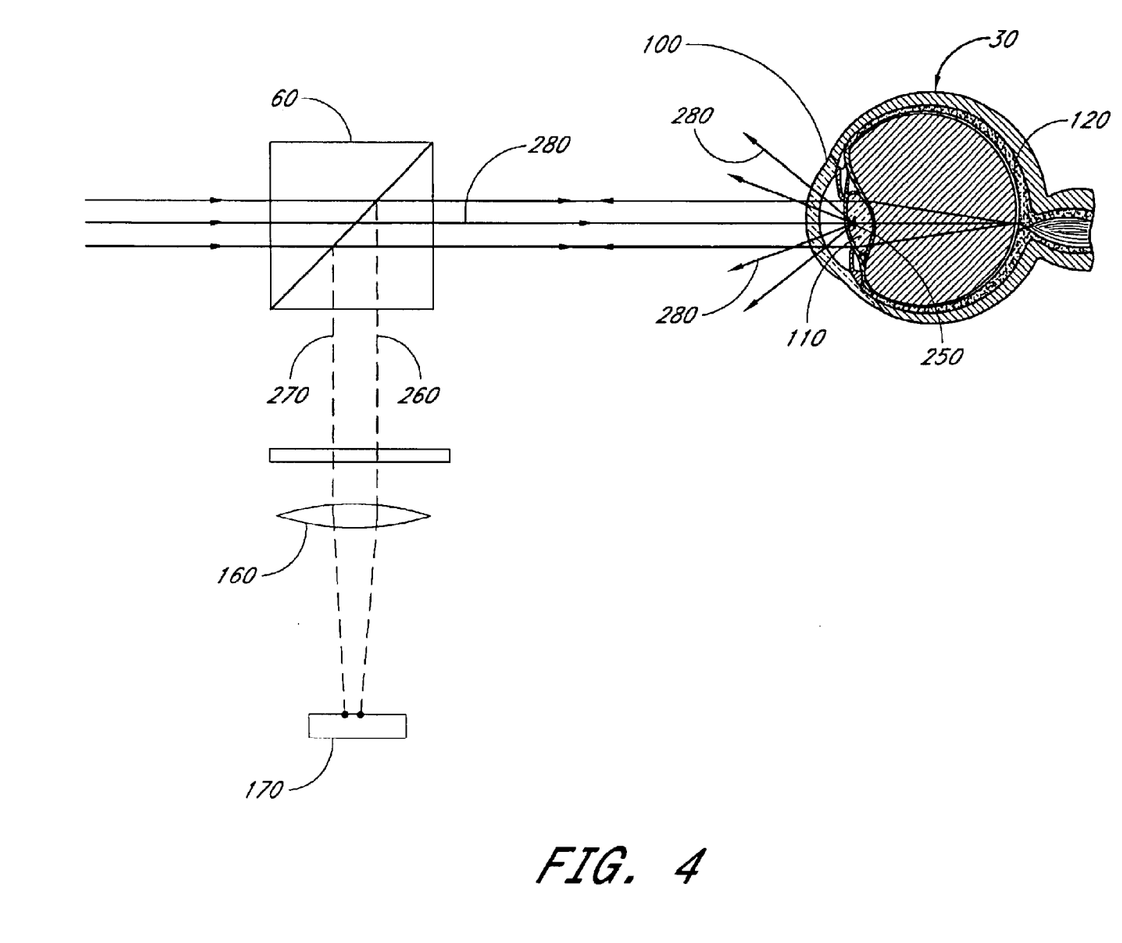

However, light directly from the light source 40 that is back-scattered by cataractous regions 250 of the ocular lens 110, such as illustrated by ray 280 does not travel in a narrow beam, but rather spreads out in proportion to the square of the distance to the eye. Therefore, if the imaging lens 160 is placed reasonably far from the eye 30 and has a diameter not much larger than the pupil 140 of the eye, it will catch almost all of the non-scattered rays from the retina but only a small proportion of the rays back-scattered by the ocular lens 110, as illustrated in FIG. 4. As a general rule, to minimize backscatter that causes diminished contrast while not discarding relevant information, the size and location of the second lens 160 (in millimeters) can be provided by the following equation:

$$L.D.=P.D.+(D\times S)/17$$

where L.D is the diameter of the second lens 160 (or the diameter of the entrance pupil of this second lens), P.D. is the pupil diameter, D corresponds to the length of the optical path from the eye 30 through the beamsplitter 160 to the second lens, S is the diameter of the image of the light source 40 on the retina 120. The value 17 in the equation originates from the focal length of the cornea 100 and ocular lens 110, which is on average about 17 millimeters. Since this equation includes the variable, S, the size of the spot on the retina 120, the lens diameter L.D. therefore depends on the size of the light source 40, the focal length of the first lens 50 and the sharpness of the focus of the image of the light source on the retina 120.

In one preferred embodiment similar to that shown in FIG. 1, the distance from the eye to the imaging lens 160 is about 200 mm and the diameter of second lens 160 is about 20 mm. This geometry reduces the relative strength of the back-scattered light to a negligible level.

Figure 5:
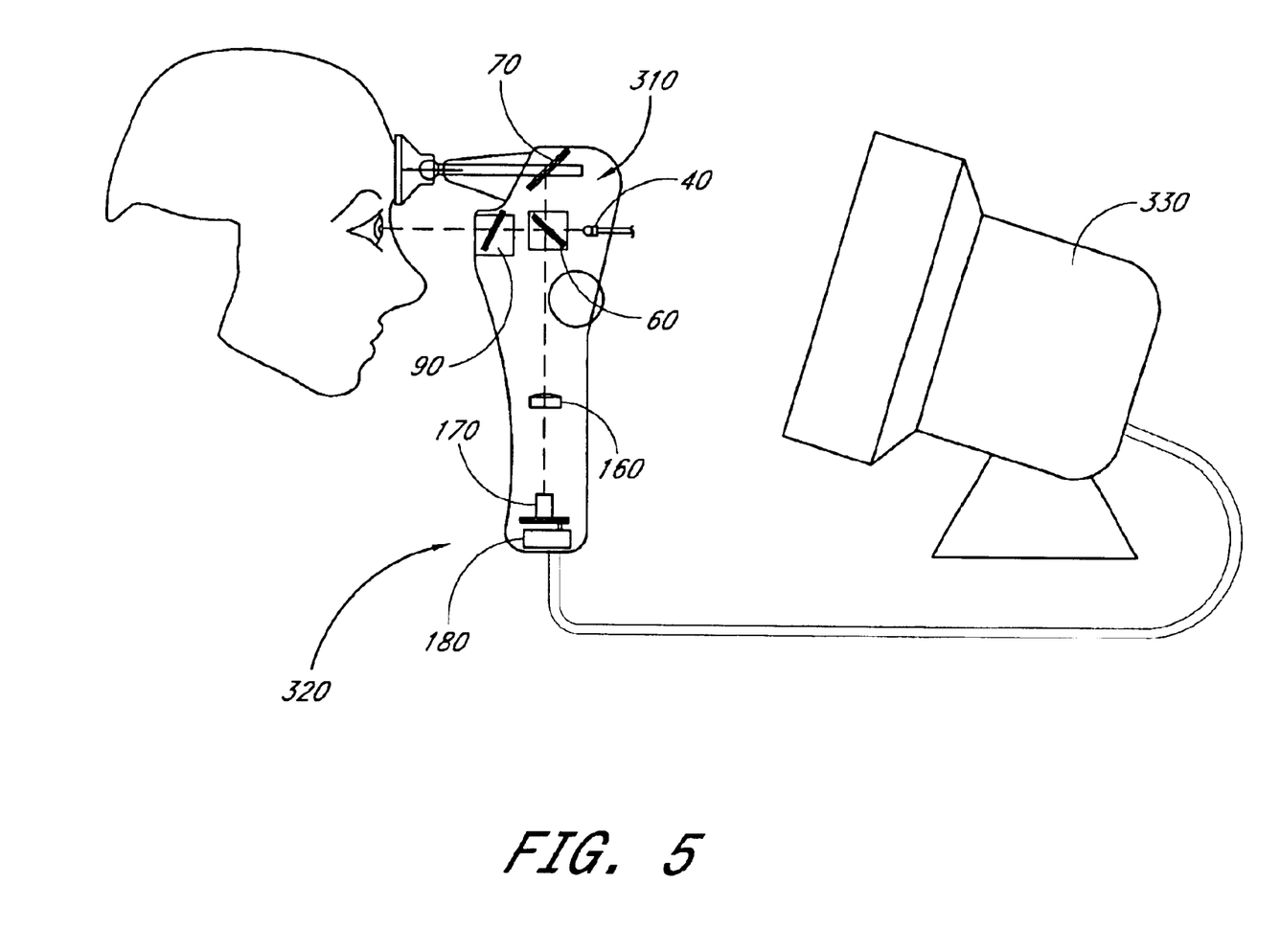
FIG. 5 depicts an embodiment comprising a hand-held optical assembly that includes the light source, the beamsplitter, lenses, and an optical detector electrically connected to a video or computer monitor for real time viewing by a cataract patient.

The instrument may or may not include a computer or microprocessor and associated software. In one embodiment, an instrument without a computer, includes the optical system 310 such as the one shown in FIG. 1 in an enclosure that permits its use as a hand-held instrument 320, and a video monitor 330, as shown in FIG. 5. Preferably, this instrument weighs between about ¼ pound to two pounds and is sufficiently compact in size and weight so as to be conveniently held by hand in front of the patient's face by the practitioner preferably without excessive vibration or other movement that reduce the accuracy of the measurement or make their acquisition substantially difficult. Preferably, the monitor 330 is placed in front of the patient so that the patient and examiner can view the cataract as a substantially live or close to real time image, i.e., while the eye 30 is being imaged, (and with an optional printer, images can be saved as hard copy). In this way, the patient and examiner can discuss the cataract. Electronics for providing power, e.g., to the light source 40 and the optical detector 170 and for receiving signals corresponding to the image and converting to electronic (e.g., video) signal compatible with the display device 330 are not shown.

Another embodiment includes the optical system 10 in FIG. 1 plus a computer 180, monitor or screen 190, and keyboard. In this version, the patient may view the computer monitor or screen 190, where the cataract image is displayed. In addition, when the examiner presses a button, the image is captured and analyzed in the computer 180, as discussed below.

The instrument 20, however, need not be hand-held. In another embodiment, the optical and electronic components (maybe with the exception of the monitor/display device 190) can be mounted in a table-top fixture that allows adjustment of the position in x,y,z to align with the patient's eye 30, and has a fixture that supports the patient's head and chin. Alternatively, the hand-held device can also be inserted into a table-mounted adjustment and head-positioning fixture. Various other arrangements and configurations are also considered possible and are not limited to those described herein.

In various embodiments, the detector signals from the camera 170 are digitized and captured in a computer 180. An array of numbers results, which represents the cataract image, and which is analyzed to generate a quantification of the cataract.

As is well known, the pupil 140 of the eye 30 is the roughly circular hole in the iris 130 through which light passes to form the retinal image. Any cataractous region 250 that lies outside that area, that is, that lies behind the iris 130, for example, has no effect on vision and is preferably excluded from the quantification.

Three aspects of the cataract are relevant to its effects on the patient's vision, (i) the degree or strength of scatter at each point in the pupil 140, (ii) the size of the area on the pupil covered by regions 250 that scatter, and (iii) the locations of those regions within the pupil. Preferably the method of analysis takes some or all of these aspects into account.

As explained above, the amount, degree, or strength of scatter at each point in the image of the pupil 140 is directly related to the darkness of the pupil image at the corresponding point. Similarly, because scattered light falling on the retina 120 impairs vision, the darkness of each point in the pupil image is directly related to the degree to which the associated location in the ocular lens 110 scatters light and interferes with vision. Further, the more such points in the pupil image, the greater the total scattered light and thus the greater the visual impairment.

Image analysis may therefore be performed as follows. First, the image may be analyzed to find the edges, spatial bounds, or extent of the pupil 140 and center or centroid of the pupil 140. Methods for determining the edge and center are explained below. In one case, a set of concentric circles may be drawn, centered on the center of the pupil. For example, the smallest circle may have a diameter of about 2 millimeters at the pupil width. Larger circles may each increase in diameter, for example, by one about millimeter until they fill the pupil. (See the circular demarcations in FIG. 7.) In one exemplary embodiment, separate analyses of each of these circular regions may be performed, as explained below. Other approaches may also be employed in other embodiments.

It may be assumed that the brightest region within the image of the whole pupil represents a part of the pupil that is clear, that is, is without significant cataract. (That assumption will certainly be wrong for some patients, but those are likely to be patients with cataracts that impair vision enough that analyzing them is moot.) The mean signal (e.g., video) level of this high intensity (peak) region is taken as a reference value, call it $V_{max}$.

One small region at the corner of the video sensor or optical detector may be blocked so that no light can fall on it. The signal level of that blocked region may be saved as a reference $V_{min}$. Then every point in the image that lies within the outer computed boundaries of the pupil is assigned a value C(x,y);

$$C(x,y)=100\times(V(x,y)-V_{min})/(V_{max}-V_{min})$$

where V(x,y) is the signal (e.g., the video signal) level at point (x,y) on the detector array in the camera 170. In one embodiment the array comprises a plurality of rows and columns of optical sensors, x and y corresponding to positions along the rows and columns in the array.

For example, if $V(x,y)=V_{max}$, then $C(x,y)=100$ (%), that is, the degree of scatter at point x,y is theoretically zero—there is no cataractous material associated with that location. If $V(x,y)=V_{min}$, then $C(x,y)=0$. This condition is approached as the cataract scatters more and more strongly.

A set of numbers quantifying the cataract is generated by computing a value associated with the area within each of the concentric circles. This number is N(c):

$$N(c) = 100 - \frac{\sum_{0}^{NP(c)} C(x, y)}{NP(c)}$$

where NP(c) is the total number of pixels within the circle c.

Thus N(c) for a given circle c is the percent of the maximum possible scatter within that circle, and so represents the degree to which the area within that circular portion of the pupil 140 degrades the contrast in the retinal image. N(c) is a measure of the reduction in the optical contrast of the retinal image caused by a given circle region c. However, the visual effect of scattered light can also be represented by a modification of the method for computing N(c), as follows.

The eye 30 can be characterized by a phenomenon called the Stiles-Crawford Effect. Because of the configuration of the photoreceptors in the center of the human retina 120, light passing through the center of the pupil 140 is substantially more effective in activating the photoreceptors than is light passing through the edges of the pupil. Therefore, light scattered from a cataract at the center of the pupil 120 will reduce the perceptual contrast of the image more strongly than light scattered from regions away from the center.

Thus, in addition to the set of numbers labeled N(c), a second set of numbers may be computed, labeled SC(c), in which each of the measures of strength of scatter, for each of the points, is weighted by its distance from the center of the pupil. In one embodiment, the weights preferably having values determined by the known parameters of the Stiles-Crawford Effect.

$$SC(c) = 100 - \frac{\sum_{0}^{NP(c)} C(x, y) \times SC(r)}{NP(c)}$$

where SC(r) are the weights for each location on the image corresponding to a point on the ocular lens 110 and r is the distance (i.e., radius or radial separation) from the pupil center to the point (x,y).

In one exemplary method for finding the center of the pupil, points in the image that are likely to represent the edges of the pupil are located. To accomplish this step, a histogram of the values of all the pixels in the image may be computed. This histogram will likely have the general appearance shown in FIG. 6A. A first large peak 350 at low values represents the dark background 210 surrounding the pupil image 200 (see e.g., FIG. 2). A second rise and peak 360 represents the value within the pupil image 200. A threshold 370 for identifying pixels associated with the pupil image 200 is also shown.

Figure 6A:
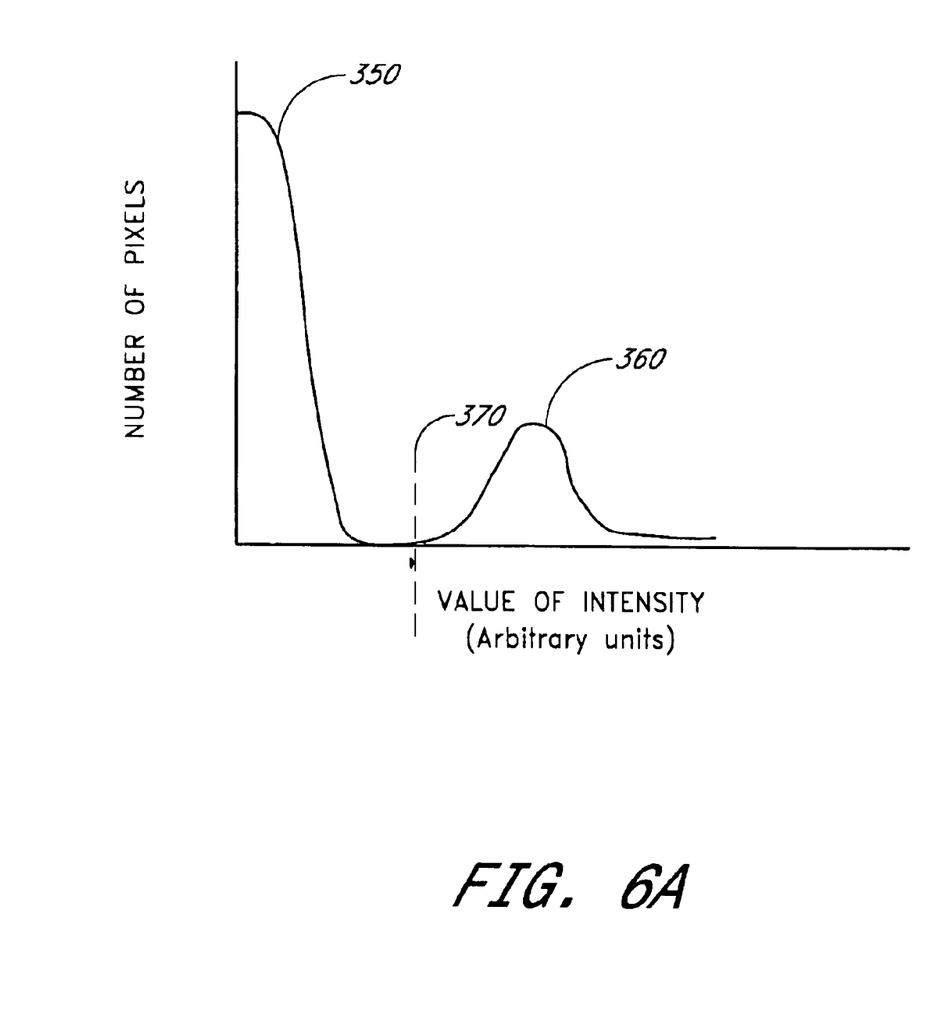
FIG. 6A is a histogram on axes of number of pixels versus value of intensity showing a peak corresponding to the pupil of the eye and a peak corresponding to background surrounding the pupil image.

In one embodiment, this threshold 370 can be employed to determine the edges of the pupil. The location(s) where the signal value changes from below to above the threshold can be saved and the location where the signal value changes from above to below can also be saved when progressing across a line of pixels. These locations constitute the initial estimates of the locations of the edges of the pupil image. These points are referred to as "edge points."

Figure 6B:
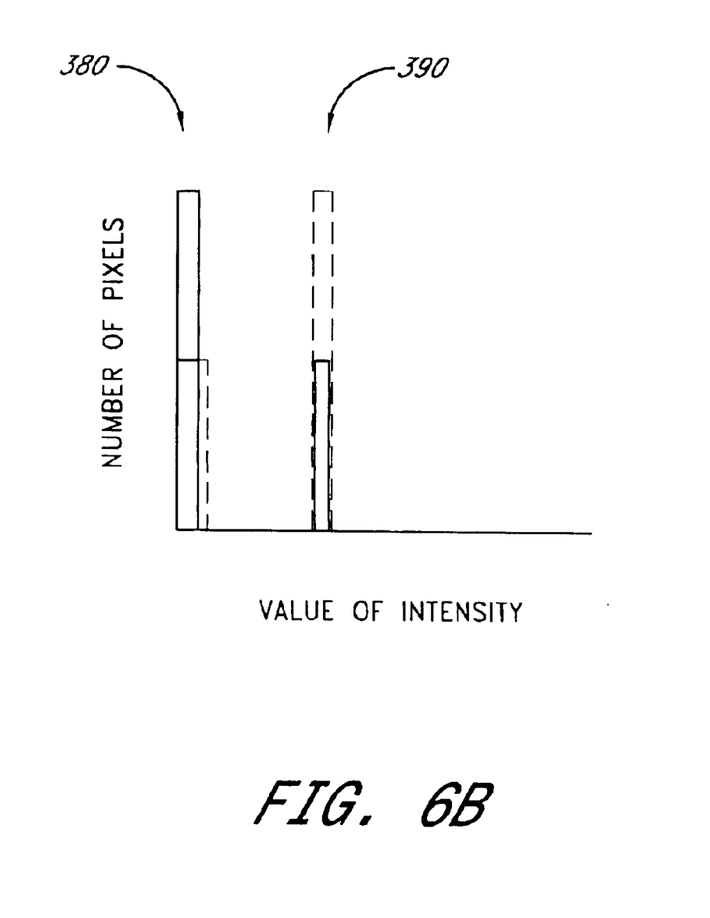
FIG. 6B is a histogram on axes of number of pixels versus value of intensity also showing a peak corresponding to the pupil of the eye and a peak corresponding to background surrounding the pupil image for a special idealized case.

A histogram for a simplified example is illustrated in FIG. 6B for an idealized image in which all of the portions of the optical image not occupied by the (bright) pupil region 200 are completely dark and all pixels within the pupil image 200 have identical (high) values. Then the histogram will be as illustrated in FIG. 6B, where again a first lower value peak 380 corresponds to the dark background 210 surrounding the pupil image 200 (see, e.g., FIG. 2) and a second higher value peak 390 corresponds to the pupil image 200. A solid line represents the plot for a relatively small pupil 140 and the dashed line represents the plot for a relatively larger pupil 140.

Figure 6C:
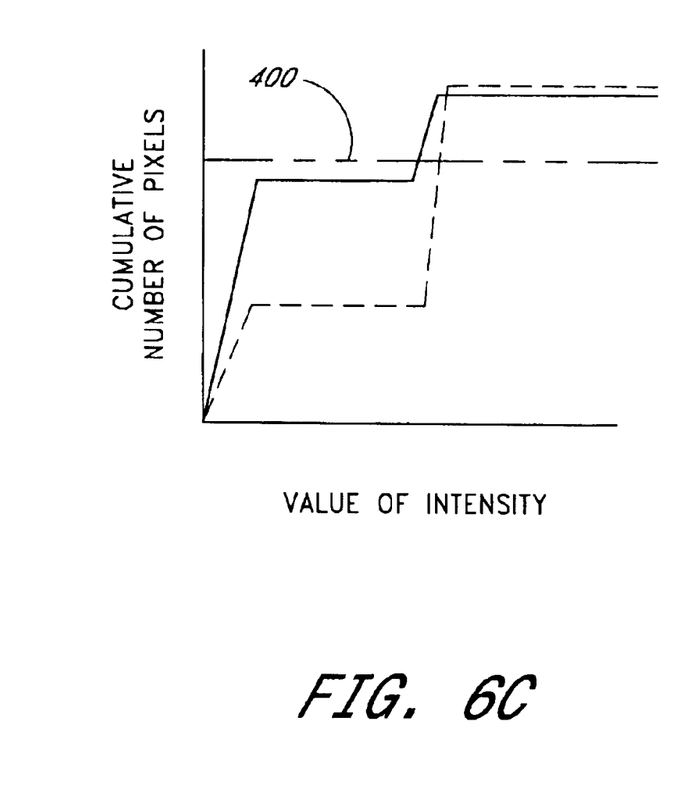
FIG. 6C is a plot on axes of cumulative number of pixels versus value of intensity showing how a threshold value of pixel intensity can be acquired to aid in determining the center and edges of the pupil.

The integral of the histogram may then be calculated producing a distribution as shown in FIG. 6C. From this plot the total number of pixels with values equal to or less than a specific signal level can be determined for the full range of signal levels obtained. As in the case described above with reference to FIG. 6B, a solid line represents the plot for a relatively small pupil 140 and the dashed line represents the plot for a relatively larger pupil 140.

In one example, the smallest pupil typically encountered has an area of about 7 square millimeters. For a typical CCD camera and an exemplary magnification, this size pupil will occupy about 15,000 pixels. An intensity value between the bright pupil pixels (15,000) and the darker background pixels can be determined with a horizontal line 400 at the level in the plot FIG. 6C where the cumulative number of pixels equals the total number of pixel (both bright and dark) subtracted by the 15,000 brightest pixels. The signal value where this level intersects the histogram is an estimate of the signal level or brightness representing a transition from the darker background region 210 to that of the bright pupil area 200 of the image.

An estimate of the location of the center of the pupil can be computed as follows. The mean of the horizontal positions of all pixels with values higher than the transition value is taken as an initial estimate of the horizontal position of the pupil center, and likewise for the vertical position.

To determine the edge of the pupil, virtual lines are drawn outward, radially, from this estimated center point every α degrees, for example every 5 degrees. For each of these lines, the point where the value first changes from above to equal to or below the transition value is taken as an estimate of the location of a point on the edge of the pupil. These locations may also correspond to the "edge points". Other techniques for determining the center, spatial extent, and/or edges or boundaries of the pupil may also be employed in various other embodiments and the method is to not be limited to those described herein.

If there were no cataractous material in the image of the pupil, then the image of the pupil would simply be a circle or ellipse, and automatically finding its center would be more simple. For example, the horizontal and vertical positions of the center could be taken as the means of the horizontal and vertical positions of the edge points. However, if there are dark regions that result from cataractous material, they will also generate edge points, but points that are not edges of the pupil, thus degrading the accuracy of that simple method.

Another method for determining the center of the pupil comprises creating list containing all of the "edge points", each point having an "x" and a "y" location, the total number of edge points in the list being designated N. A number of edge points, for example, five points are selected from the list at random, with the constraint that no two points can lie closer together in the list than, for example, N/10 positions. (If there were no cataractous points, this would mean that the edge points selected would not be close together around the edge of the pupil.) The x,y locations of five points in a plane are sufficient to specify an ellipse in that plane. The next step, then, is to find the x,y location of the center of the ellipse defined by those five points. This procedure is repeated for many, e.g. 50, selections of five points, and the x,y location of the pupil is taken as the median of the x and y values of the centers of the (50) ellipses. A different number of edge points other than 5 can be selected and the procedure can be repeated more or less than 50 times in other embodiments.

Note that the methods recited above are not to be construed as limiting, as other techniques for determining the edges, centers, and spatial extent of the pupil can be employed. In addition, the method need not be carried out in any particular order, the sequence in the methods described above are merely exemplary.

Figure 7:
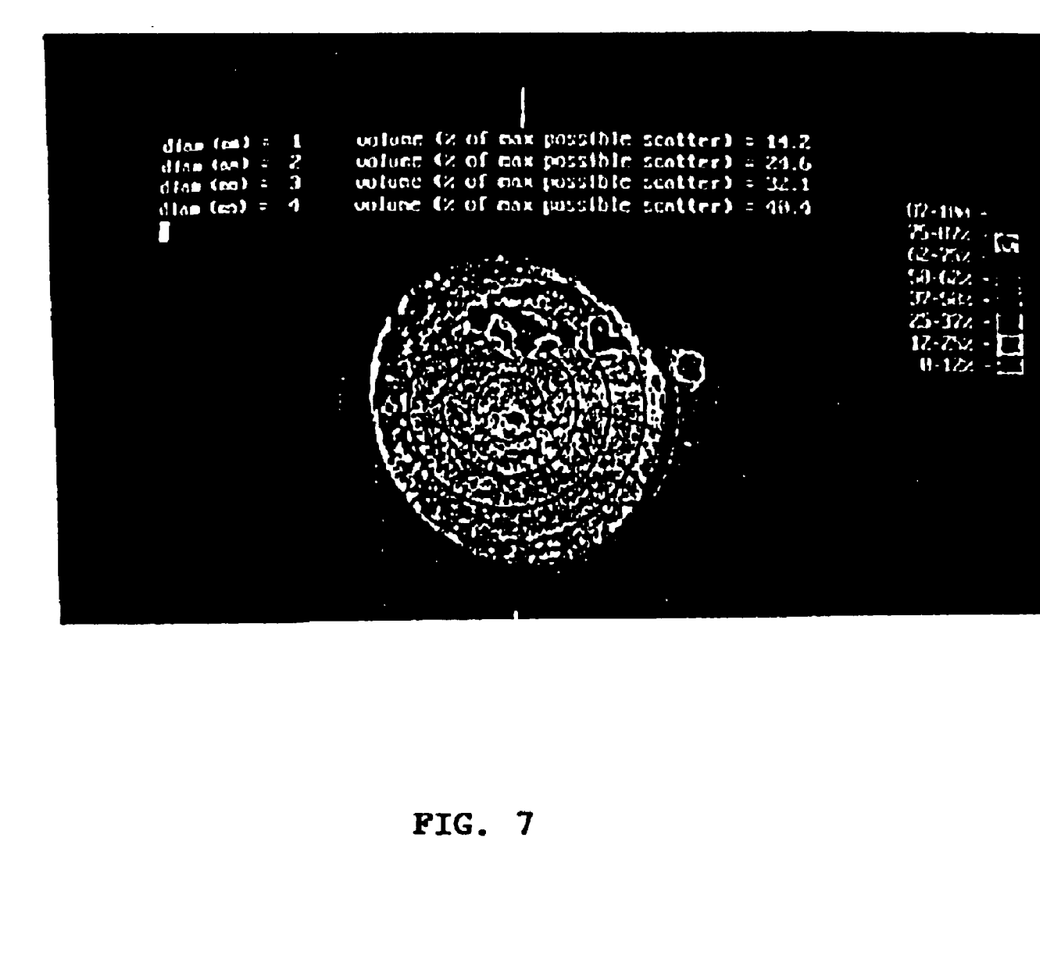
FIG. 7 depicts a screen displayed on the TV or computer monitor showing an image of the cataract in the pupil along with a table of numbers quantifying the cataract.

Results can be displayed on the computer screen or other display device and can be printed. The display shown in FIG. 7 comprises two parts. One part is a map of the ocular lens 110 and cataract 250, with the cataract strength at each point color-coded. The strength is a plot of C(x,y). In other embodiments, this image displayed may be a colored (or pseudocolored) or monochrome. The second is a table of numbers, the values of N(c) and SC(c). Concentric circles are shown in FIG. 7.

FIG. 5 is a drawing of one preferred embodiment of the instrument, a hand-held version. During operation, the operator rests a support against the patient's forehead above the eye 30 to be examined, and, while watching the display screen, moves the instrument 320 until an image of the pupil 140 is approximately centered on the screen. Turning a knob moves the imaging lens 160 and/or camera 170 upward or downward to bring the pupil 140 into sharp focus. The patient may also view the display 330 while the patient and examiner discuss the cataract 250.

In the version that includes a computer or other electronics 180 to analyze and display results, the optical head may also contains a button which, when pressed, causes the computer to capture the image and analyze and display it. For this version, when the examiner wishes to capture an image for analysis, the patient can be asked to look straight into the optical system 10 of the instrument 320 rather than at the monitor 330 (so that the appropriate part of the ocular lens 110 is imaged).

Note that many other applications of the apparatus and methods are considered possible; the relevant applications not being limited to those specifically recited above. Also, the present invention may be embodied in other specific forms. The embodiments described above are to be considered in all respects as illustrative only and not restrictive in any manner.

What is claimed is:

1. A method of quantifying the extent a cataract impairs vision in an eye having a pupil, an ocular lens containing the cataract, and a retina, said method comprising:
    illuminating a localized region of the retina such that light is reflected from the localized region and is transmitted through the ocular lens, a portion of the reflected light being scattered by the cataract contained within the ocular lens;
    collecting a focused image of the ocular lens from the light reflected from the localized region of the retina; and
    measuring the amount of scatter in the image of the ocular lens to quantify the extent the scatter impairs vision of the eye.

2. The method of claim 1 including the step of directing the collected light onto a light-sensitive detector having an output indicative of the light intensity incident thereon.

3. The method of claim 2 including the step of forming an optical image of the ocular lens on the light-sensitive detector.

4. The method of claim 3 including the step of reducing the size of the illuminated region of the retina to increase the contrast of the image of the ocular lens.

5. The method of claim 4 wherein the localized region that is illuminated in the range of about 0.05 to about 0.3 millimeter (mm) in size.

6. The method of claim 2 including the step of computing a figure of merit based on the output from the light-sensitive detector to assess the extent the cataract impairs vision.

7. The method of claim 2 wherein the light-sensitive detector has an electrical output indicative of light intensity incident thereon, and including the step of processing the electrical output to quantify the amount of scatter.

8. The method of claim 6 further including the steps of forming an optical image of the ocular lens having the cataract on the light-sensitive detector and displaying an electronic image of the ocular lens of the eye on an electronic display using the output from the light-sensitive detector.

9. The method of claim 8 including the step of positioning the electronic image to be visible by a patient while the optical image of the eye is being formed on the light-sensitive detector.

10. The method of claim 8 including the step of accommodating viewing by the patient of the electronic image while the optical image is being formed on the light-sensitive detector.

11. A method of quantifying the extent a cataract impairs vision in an eye having a pupil, an ocular lens containing the cataract, and a retina, said method comprising:
    illuminating a localized region of the retina such that light is reflected from the localized region and is transmitted through the ocular lens, a portion of the reflected light being scattered by the cataract contained within the ocular lens;
    collecting a focused image of the ocular lens from the light reflected from the localized region of the retina;

measuring the amount of scatter in the image of the ocular lens to quantify the extent the scatter impairs vision of the eye, said step of measuring the amount of scatter comprising the step of directing the collected light onto a light-sensitive detector having an output indicative of the light intensity incident thereon;

computing a figure of merit based on the output from the light-sensitive detector to assess the extent the cataract impairs vision;

forming an optical image of the cataract on the light-sensitive detector;

displaying an electronic image of the eye on an electronic display using the output from the light-sensitive detector; and summing the relative amount of scatter for different portions of the electronic image.

12. The method of claim 11 including the step of further forming substantially concentric circles centered within the pupil and corresponding with the different portions of the electronic image.

13. The method of claim 12 including the step of further computing a value for the figure of merit that includes scaling the contribution of scattered light associated with a region of the pupil by a factor that depends on proximity to a center of the pupil.

14. A method of imaging a cataract in an eye having a cornea, an ocular lens, and a retina, said method comprising the steps of:

holding an assembly comprising a light source, imaging optics, and an optical detector array in place by hand a distance from the eye;

illuminating a localized region of the retina with light from the light source such that at least a portion of the light is reflected from the localized region of the retina through the ocular lens;

collecting a focused image of the ocular lens from the light reflected from the localized region of the retina with an optical element;

forming an optical image of the cataract on the optical detector array with imaging optics to produce an electronic image of the cataract; and displaying the electronic image of the cataract on a display.

15. The method of claim 14 including the step of showing the patient the electronic image of the eye when the assembly is held in place close to the eye to capture the electronic image of the cataract.

16. The method of claim 15 wherein said step of showing is carried out simultaneously with the formation of the optical image on the optical detector array.

17. The method of claim 14 including the step of reducing reflection from the cornea by providing a polarizing filter.

18. The method of claim 17 including the step of providing polarizing filtering with a polarizing beamsplitter.

19. The method of claim 18 including the step of positioning a polarizer between the beamsplitter and a source of light for illuminating the eye and the step of further positioning an analyzer between the beamsplitter and the optical detector array.

20. The method of claim 14 including the step of reducing the collection of rays scattered from the cataract by the imaging optics by selecting the imaging optics to have a small aperture.

21. The method of claim 20 including the step of selecting the imaging optics to have an aperture in the range of about 10 to about 30 millimeters (mm) in diameter.

22. The method of claim 21 including the step of reducing the collection of rays scattered from the cataract by the imaging optics by positioning the imaging optics to provide an optical path length from the eye to the imaging optics in the range of about 100 to about 400 millimeters.

* * * * *